United States Patent [19]

Sweere

[11] Patent Number: 4,743,237

[45] Date of Patent: May 10, 1988

[54] CONTAINER HAVING SECURELY-ATTACHED HANDLING CORD AND METHOD AND APPARATUS FOR PRODUCING THE CONTAINER

[75] Inventor: Douglas D. Sweere, Neenah, Wis.

[73] Assignee: Kimberly-Clark Corporation, Neenah, Wis.

[21] Appl. No.: 943,569

[22] Filed: Dec. 18, 1986

[51] Int. Cl.$^4$ .............................................. A61F 13/16
[52] U.S. Cl. ..................................... 604/358; 604/904
[58] Field of Search ................................ 604/904, 358

[56] References Cited

U.S. PATENT DOCUMENTS

| 3,520,302 | 7/1970 | Jones | 128/285 |
| 3,736,935 | 6/1973 | Reimels | 128/296 |
| 4,335,721 | 6/1982 | Matthews | 604/904 |
| 4,624,668 | 11/1986 | Siegers | 604/904 |
| 4,642,108 | 2/1987 | Sustmann | 604/379 |

FOREIGN PATENT DOCUMENTS 2423790 11/1975 Fed. Rep. of Germany ...... 604/904
3347649 7/1985 Fed. Rep. of Germany .

Primary Examiner—John D. Yasko
Attorney, Agent, or Firm—Paul A. Leipold; Donald L. Traut; Jeremiah J. Duggan

[57] ABSTRACT

The invention provides a method and apparatus to wrap a filler material with a porous gauze and attach a handling cord. The gauze material is thermoplastic and is heat sealed around the filler material. A string is then pierced through the gauze wrapping in a location exterior to the filler. The sides of the wrapping are then brought together surrounding the pierced string or cord to fuse the cord to the wrapping gauze.

In a preferred form, the filler material is an absorbent for a tampon. After the fusing of the tampon withdrawal cord to the wrapping material, the tampon is compressed to the size conventionally utilized for a tampon and may be utilized either in a digital or applicator-type tampon.

8 Claims, 4 Drawing Sheets

CONTAINER HAVING SECURELY-ATTACHED HANDLING CORD AND METHOD AND APPARATUS FOR PRODUCING THE CONTAINER

FIELD OF THE INVENTION

This invention relates generally to a method of forming a container having a securely-attached handling cord. It particularly relates to the formation of tampons having a thermoplastic gauze outer wrapping with the withdrawal cord thermoplastically bonded to the gauze.

DESCRIPTION OF THE PRIOR ART

Intervaginal tampons are in common use by women for the retention of fluid or menses discharged along the walls of the vagina during the menstrual cycle. Such tampons are usually formed of absorbent material such as cotton, rayon, cellulose wadding, synthetic sponge, cellulose fluff, synthetic fibers or combinations of these materials compressed or molded usually to a generally cylindrical configuration of a size to fit within the vaginal tract.

Intervaginal tampons may be inserted either by the use of applicators, which eject the tampon within the vagina, stick insertion or by digital insertion within the vagina. Tampons are generally provided with a withdrawal cord or string that is utilized to withdraw the tampon from the vagina. The attachment of the string to the tampon is critical in that it is necessary that the string be attached in such a manner that the tampon is withdrawn from the vagina in one piece. Further, the string or withdrawal cord must be attached in such a manner that it is not susceptible to becoming unattached from the tampon such that the tampon may not be easily removed from the vagina.

Methods of attachment of the withdrawal cord to tampons have included passing a string through the tampon and knotting the string after it has passed through the tampon. However, this system is subject to failure if the knot is not perfectly formed or becomes untied. It has been proposed in U.S. Pat. No. 1,731,665—Huebsch and U.S. Pat. No. 2,710,007—Greiner et al. that the gauze overwrapping of a tampon be extended and utilized as a withdrawal cord. A disadvantage of this system is that the gauze overwrapping material is more expensive than a cord and further, forms a larger withdrawal device that is not preferred by women. Further, the gauze covering, in addition to being thicker, it has more of a tendency to wick fluid, which is undesirable in a tampon withdrawal cord.

Therefore, there remains a need for a method of quickly attaching a withdrawal cord to a tampon in such a manner that it will not come loose under any conditions.

BACKGROUND OF THE INVENTION

An object of the invention is to overcome disadvantages of prior tampons and cord attachment means for tampons.

Another object of the invention is to provide an efficient, low-cost method and apparatus for forming tampons with securely-attached cords.

A further object of the invention is to form containers having a securely-attached handling cord.

These and other objects are generally accomplished by providing a method and apparatus to wrap a filler material with a porous gauze. The gauze material is thermoplastic and is heat sealed around the filler material. A string is pierced through the gauze wrapping in a location exterior to the filler. The sides of the wrapping are then brought together to surround the pierced string or cord and by heat and pressure fuse the cord to the wrapping gauze.

In a preferred form of the invention, the filler material is an absorbent for a tampon. After the fusing of the cord to the wrapping material, the tampon is compressed to the size conventionally utilized for a tampon and may be utilized either in a digital, stick or applicator-type tampon.

MODES FOR CARRYING OUT THE INVENTION

The invention has many advantages over the prior tampons and method and apparatus for forming such tampons. An advantage of the instant tampon is that the withdrawal string will not come loose. Another advantage is that the fastening of the draw string to the cover for the tampon is simple, low cost and reliable as heat and pressure are all that is required. These and other advantages of the invention will become apparent from the detailed description of the invention below.

Figure 1:
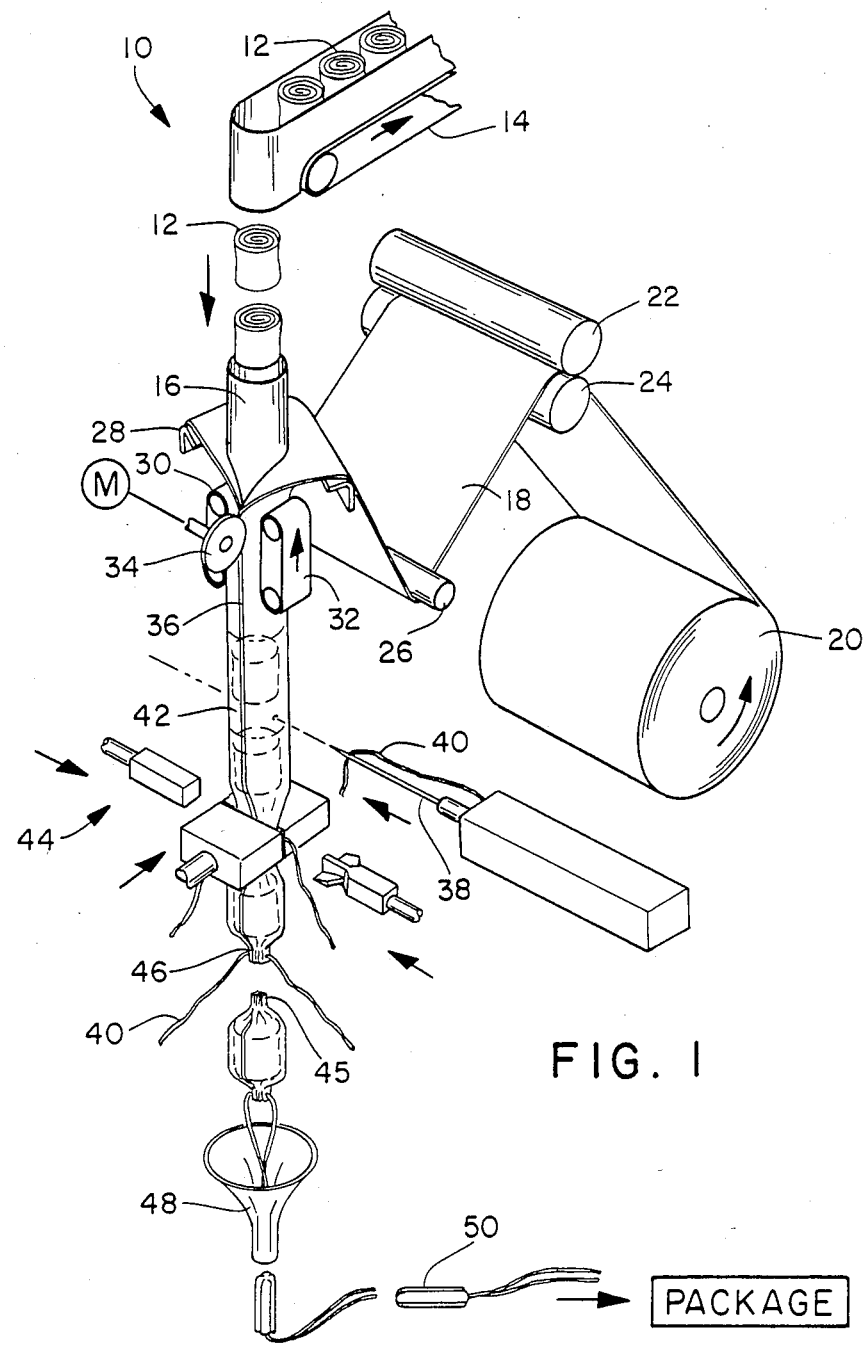
FIG. 1 is a perspective view of an apparatus and method for performing the invention.

FIG. 1 illustrates the apparatus 10 for performing the method of the invention to form the tampons of the invention. The conveyor 14 intermittently feeds filler members 12 to the apparatus. The fillers 12 are rolled absorbent members. The fillers 12 drop into the feding tube 16. Around the filler tube 16 there is wrapped gauze 18 that is supplied from roll 20. The gauze material 18 passes over the feed rolls 22, 24 and 26 that control its tension. The gauze passes over folding member 28 that aids in its being wrapped around the feed tube 16. The gauze wrapper is moved by driven belt apparatus 30 and 32 that drives the gauze 18 as the belt apparatus 30 and 32 presses the gauze against the feed tube 16. Heat sealing wheel 34 fuses the edges of the gauze sheet 18 together on line 36. As the absorbent fillers 12 exit tube 16, after being wrapped with gauze 18, the gauze cylindrical casing is pierced by reciprocating needle 38 carrying cord 40. Cord 40 is supplied from a source of continuous cord, not shown, and is cut off by cutter, not shown, after piercing through the cylindrical cover 42. Reciprocating needle 38 pierces covering 42 between fillers 12 and the cord is cut off such that is is freely hanging on each side of the cylindrical casing 42. After the cord 40 has pierced the casing 42, it moves to heat sealing and cutting unit 44 where the cylindrical casing 42 and cord 40 are compressed and sealed together. The compressed seal is cut into cord bearing lower seal 46 and cord-free upper seal 45 in sealing unit 44 and exits the sealing apparatus 44. The tampon preform enters the compression device 48 where the tampon preform is compressed to form compressed tampon 50. The tampon 50 may then be packaged for shipping and sale.

Figure 2:
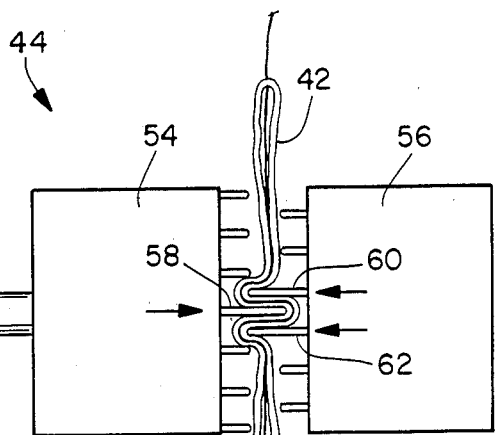
FIGS. 2-5 illustrate the apparatus for fusing the cord to the wrapper.
Figure 3:
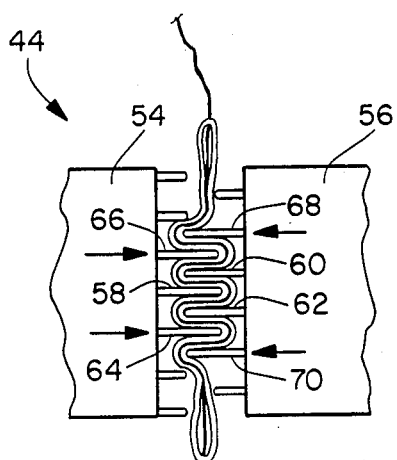
Figure 4:
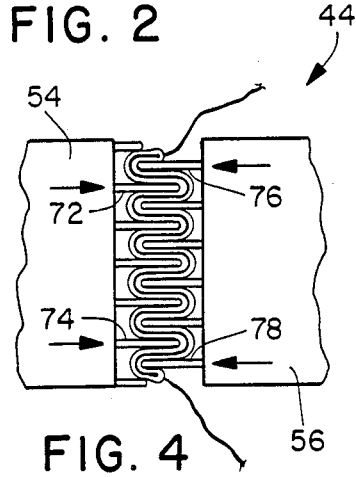
Figure 5:
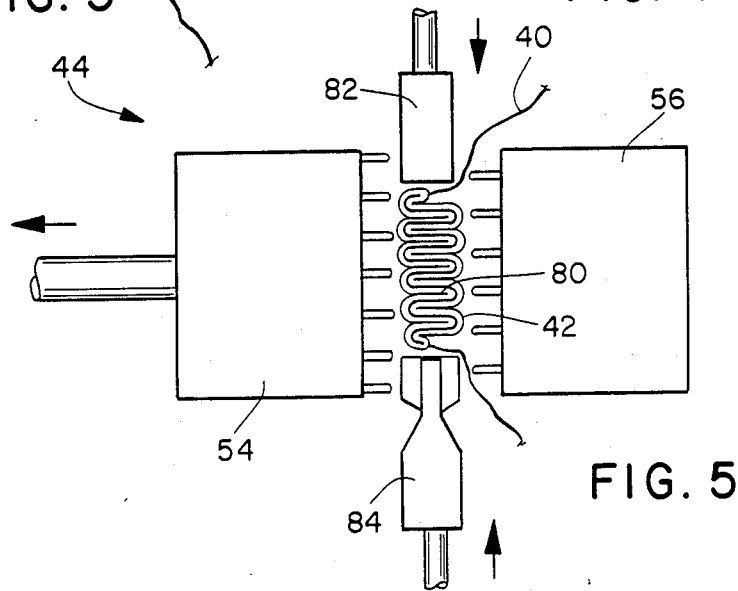

FIGS. 2-5 show the sealing and cutting apparatus 44 in greater detail. In the sealing of the cord end and upper end of the tampon, an accordian-like fold is first formed. The heat sealing anvils 54 and 56 are provided with interlocking pins. As shown in FIG. 2, it is necessary that the centermost pins be extended when the anvils 54 and 56 are first brought towards each other in order to gather the extra material necessary for the fan fold formed between pin 58 of anvil 54 and pins 60 and 62 of anvil 56. Then sequentially the next outermost pins 66 and 64 of anvil 54 and pins 68 and 70 of anvil 56 are brought together. Lastly the moveable pins 72 and 74 of anvil 54 and moveable pins 76 and 78 of anvil 56 are brought into contact. After the fan-folded seal 80 is formed, it is compressed and cut by heated anvils 82 and 84 to further seal the cord 40 into the wrapper 42.

Figure 6:
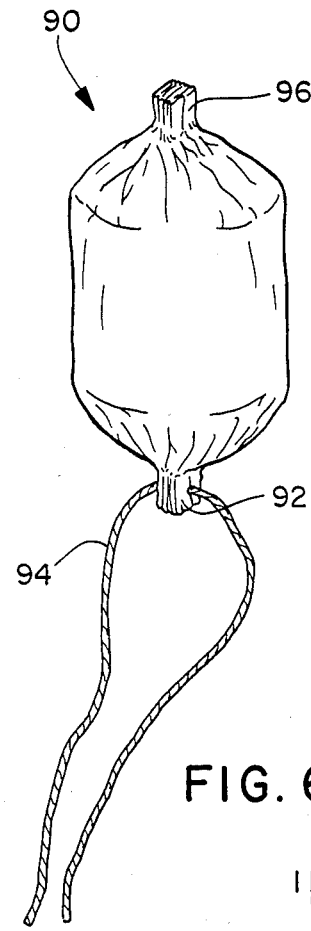
FIG. 6 is a view of a container of the invention.

FIG. 6 illustrates a container 90 of the invention that is sealed on one end with seal 92 that contains the cord 94 integrally thermally bonded into the seal 92. The container 90 also has an upper seal 96. This upper seal, with reference to FIG. 1, is formed by severing of a larger seal formed in sealing and cutting apparatus 44 into the cord containing lower seal 46 and the opposite end not cord containing seal 45. The container of FIG. 6 may represent a tampon prior to compression to form a pledget. The container of the invention also may be utilized as a container for absorption of spills or as a container for food materials such as tea.

Figure 7:
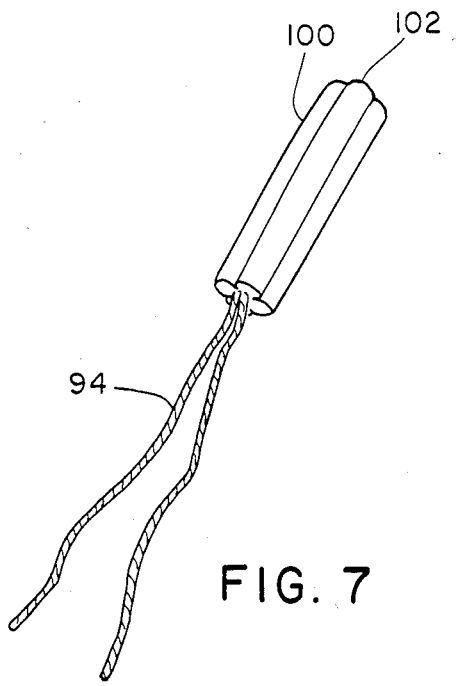
FIG. 7 is a view of a tampon of the invention.

FIG. 7 illustrates a tampon 100 formed by compression of the container of FIG. 6. The tampon 100 may be utilized in a tube-type tampon applicator. If designed for use in a stick or digital applicator tampon, the forward end 102 would be rounded for digital or stick insertion.

Figure 8:
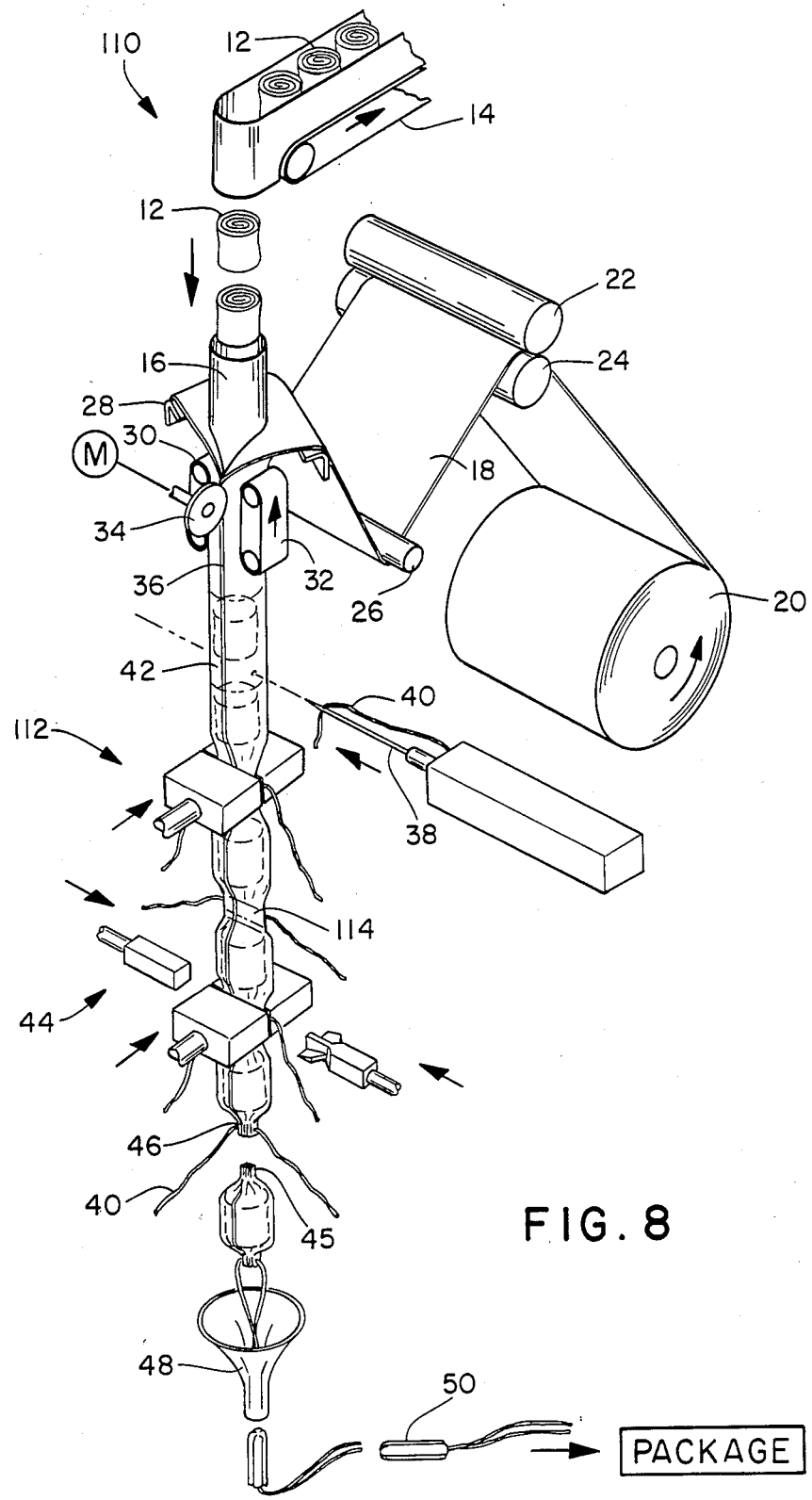
FIG. 8 is a perspective view of an alternate method and apparatus for performing the invention.

FIG. 8 is an alternate apparatus 110 of the invention. The apparatus 110 corresponds to apparatus 10 of FIG. 1 except that another fusing 112 has been added. Fusing section 112 provides a seal 114 that first seals the cover 42 to cord 40. In apparatus 110 the seal 112 is then fan folded, fused and cut in section 44. It would also be possible to cut fused area 114 in section 44 and not fan fold if a somewhat larger, less secure cord seal was satisfactory.

Figure 9:
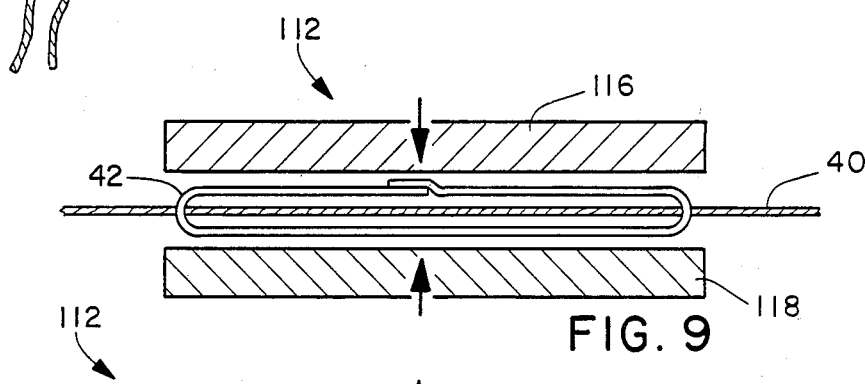
FIGS. 9 and 10 are cross-sectional views of alternate apparatus for fusing the cord to the wrapper.
Figure 10:
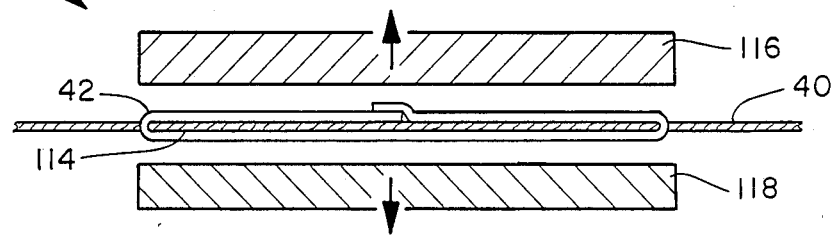

FIGS. 9 and 10 illustrate the compression and fusing of gauze cover 42 and cord 40 in the fusing apparatus 112. In FIG. 9 the cover 42 and cord 40 is being compressed by heated anvils 116 and 118 to fuse the cord 40 to cover 42. In FIG. 10 the anvils 116 and 118 separate after fusing seal 114.

While the invention has been described with continuous formation, the invention also could be utilized to seal and provide cords for individual bags of a thermoplastic material. Further, there is other apparatus that can be utilized for compression and heat sealing of the withdrawal cords and thermoplastic wrappings. For instance, the seal could be formed without a fan fold.

The withdrawal cord may be formed of any suitable material. Typical of such materials are cord or string formed of cotton as well as of polymer material such as rayon polypropylene, polyester, nylon or blends thereof. The cords and strings are less likely to wick fluid if treated with wax or silicone. However, a cotton, rayon and polyester are the preferred materials as they are low in price, soft and strong. The term cord as used herein is intended to include groups of fibers, such as twisted cotton, as well as single polymer cords.

The permeable gauze material forming the outer covering of the container of the invention may be any thermoplastic permeable material. Typical of such materials are perforated thermoplastic films and thermoplastic polymer netting materials. Preferred materials have been found to be thermoplastic spunbonded materials, particularly polypropylene spunbonded materials, as they are permeable, low in cost and fuse at lower temperatures. Further, such materials have previously been found suitable for covers for tampon materials.

The filler material for the container of the invention may be any material that is desired to contain and to manipulate with a material handling cord. Typical of such materials utilized for tampons are polypropylene, cellulose acetate, nylon, acrylic and carboxymethylcellulose. Suitable materials utilized for tampons are cotton linters, rayon and mixtures of these fibers. Any fiber that is able to be compressed for shaping into a smaller size for formation into a tampon pledget and that will expand when wet is suitable. The fiber may be folded or rolled prior to being compressed.

The cord attachment to the container is even more secure if a thermoplastic cord is utlized that has a fusion temperature somewhat near that of the wrapping material. The cord may be formed of a polypropylene material that will have a compatible fusion temperature with the preferred polypropylene spunbonded preferred cover material.

The tampons formed by the instant invention may be utilized in cardboard or plastic applicators that are inserted into the vagina prior to the tampon pledget being expelled from the container. The tampons of the invention further may be formed into stick tampons and digitally-inserted tampons.

The means for compressing the package having the string attached thereto into a tampon pledget are well known. The means generally are molds that compress the preform to the desired shaped pledget. It is beneficial if the handling of the pledget in entering and leaving such molds is by the material handling string or cord as this will automatically eliminate defective products in which the cord or cords have been severed in molding or other manufacturing processes. Packaging means for tampons are also known in the art and conventional equipment may be utilized or the tampons may be packaged by hand.

While the tampon formation has been shown with a continuous process involving the sealing of a tube at both ends in order to enclose the filler material, it is utilized that a preformed bag, open at one end, could be utilized with the stringing of the material handling cord through the open end of the bag which is then later sealed by heat and compression fusing.

While the container with the material handling string of the invention has been set forth in the preferred embodiment as a tampon, it is also possible that the apparatus and method of the invention could be utilized to form other products such as teabags. Other products that could be formed are sachets of odor-releasing compounds or potpourris of such materials. These and other uses are intended to be included by the instant invention, the breadth of which is only intended to be limited by the scope of the claims attached hereto.

We claim:

1. A container comprising a thermoplastic outer gauze covering, a filler and a handling cord wherein said cord is sealed to said container by melting and fusing said thermoplastic gauze to said cord.

2. The container of claim 1 wherein the area sealing said gauze to said cord also seals the end of said container.

3. The container of claim 1 comprising a tampon.

4. The container of claim 3 wherein said handling cord comprises a thermoplastic material.

5. The container of claim 3 wherein said gauze covering comprises a spunbonded polypropylene material.

6. The container of claim 3 wherein said handling cord passes through said covering.

7. The container of claim 1 wherein said filler comprises an absorbent.

8. The container of claim 1 wherein said seal is in a fan fold shape.

* * * * *